US00PP17619P2

(12) United States Plant Patent
Mak

(10) Patent No.: US PP17,619 P2
(45) Date of Patent: Apr. 17, 2007

(54) LILY PLANT NAMED 'TINY ICON'

(50) Latin Name: *Lilium hybrida*
Varietal Denomination: Tiny Icon

(75) Inventor: Nicolaas Aloysius Maria Mak, 't Zand (NL)

(73) Assignee: Mak 't Zand B.V., 't Zand (NL)

( * ) Notice: Subject to any disclaimer, the term of this patent is extended or adjusted under 35 U.S.C. 154(b) by 0 days.

(21) Appl. No.: 11/255,210

(22) Filed: Oct. 20, 2005

(51) Int. Cl.
*A01H 5/00* (2006.01)

(52) U.S. Cl. ..... Plt./314

(58) Field of Classification Search ..... Plt./314
See application file for complete search history.

*Primary Examiner*—Anne Marie Grunberg
*Assistant Examiner*—S. B. McCormick-Ewoldt
(74) *Attorney, Agent, or Firm*—C. A. Whealy

(57) ABSTRACT

A new and distinct cultivar of Asiatic Hybrid Lily plant named 'Tiny Icon' characterized by its small to medium plant size; vigorous growth habit; freely flowering habit; dark pink-colored tepals that are slightly recurved; and good postproduction longevity.

1 Drawing Sheet

Botanical designation: *Lilium hybrida.*
Cultivar denomination: 'Tiny Icon'.

BACKGROUND OF THE INVENTION

The present Invention relates to a new and distinct cultivar of Asiatic Hybrid Lily plant, botanically known as *Lilium hybrida,* and hereinafter referred to by the name 'Tiny Icon'.

The new Asiatic Hybrid Lily is a product of a planned breeding program conducted by the Inventor in 't Zand, The Netherlands. The objective of the breeding program was to develop new potted Asiatic Hybrid Lily plants with erect flowers, attractive flower coloration and good postproduction longevity.

The new Asiatic Hybrid Lily originated from a cross-pollination in 1996 of an unnamed proprietary Asiatic Hybrid Lily, not patented, as the female, or seed, parent with an unnamed proprietary Asiatic Hybrid Lily, not patented, as the male, or pollen, parent. The cultivar Tiny Icon was discovered and selected by the Inventor as a flowering plant within the resultant progeny of the cross-pollination in a controlled environment in 't Zand, The Netherlands in May, 1999.

Asexual reproduction of the new Asiatic Hybrid Lily by bulb scales in a controlled environment in 't Zand, The Netherlands since November, 1999, has shown that the unique features of this new Asiatic Hybrid Lily are stable and reproduced true to type in successive generations.

SUMMARY OF THE INVENTION

The cultivar 'Tiny Icon' has not been observed under all possible environmental conditions. The phenotype may vary somewhat with variations in environment such as temperature and light intensity without, however, any variance in genotype.

The following traits have been repeatedly observed and are determined to be the unique characteristics of 'Tiny Icon'. These characteristics in combination distinguish 'Tin Icon' as a new and distinct cultivar of Asiatic Hybrid Lily:

1. Small to medium plant size; vigorous growth habit.
2. Freely flowering habit.
3. Dark pink-colored tepals that are slightly recurved.
4. Good postproduction longevity.

Plants of the new Asiatic Hybrid Lily differ from plants of the parent selections primarily in plant height as plants of the new Asiatic Hybrid Lily are taller than plants of the parent selections.

Plants of the new Asiatic Hybrid Lily can be compared to plants of the Asiatic Hybrid Lily cultivar Cote d'Azur, not patented. In side-by-side comparisons conducted in 't Zand, The Netherlands, plants of the new Asiatic Hybrid Lily differed from plants of the cultivar Cote d'Azur, in the following characteristics:

1. Plants of the new Asiatic Hybrid Lily were shorter than plants of the cultivar Cote d'Azur.
2. Plants of the new Asiatic Hybrid Lily had broader leaves than plants of the cultivar Cote d'Azur.
3. Plants of the new Asiatic Hybrid Lily had lighter pink-colored flowers than plants of the cultivar Cote d'Azur.

DESCRIPTION OF THE PHOTOGRAPH

The accompanying colored photograph illustrates the overall appearance of the new Asiatic Hybrid Lily, showing the colors as true as it is reasonably possible to obtain in colored reproductions of this type. Colors in the photograph may differ slightly from the color values cited in the detailed botanical description which accurately describe the colors of the new Asiatic Hybrid Lily. The photograph comprises a side perspective view of a typical flowering plant of 'Tiny Icon' grown in a container.

DETAILED BOTANICAL DESCRIPTION

In the following description, color references are made to The Royal Horticultural Society Colour Chart, 2001 Edition, except where general terms of ordinary dictionary significance are used. The aforementioned photograph and following observations and measurements describe plants that were about two months-old and grown in 't Zand, The Netherlands under commercial practice in a glass-covered greenhouse. Plants were grown at a minimum temperature of about 15° C. and the average daylength was about 14 hours. Measurements and numerical values represent averages for typical flowering plants. The photograph and the description were taken during the early summer.

Botanical classification: *Lilium hybrida* cultivar Tiny Icon.

Parentage:

*Female, or seed, parent.*—Unnamed proprietary selection of *Lilium L.,* not patented.

*Male, or pollen, parent.*—Unnamed proprietary selection of *Lilium L.,* not patented.

Plant description:

*Plant form/growth habit.*—Upright flowering plant; single erect flowering stem with a terminal cluster of flowers. Small to medium plant size. Vigorous growth habit.

*Plant height, soil level to top of flowers.*—About 40 cm.

*Plant diameter.*—About 22 cm.

*Flowering stems.*—Diameter: About 2 cm to 2.2 cm. Internode length: About 2 mm to 5 mm. Strength: Strong. Texture: Smooth, glabrous. Color: 146B.

*Leaves.*—Arrangement: Alternate; simple; sessile. Quantity of leaves per plant: About 70. Length, lower leaves: About 6.7 cm. Width, lower leaves: About 1.2 cm. Length, upper leaves: About 8.2 cm. Width, upper leaves: About 2.9 cm. Shape: Lanceolate. Apex: Acute. Base: Attenuate. Margin: Entire. Texture, upper and lower surfaces: Glabrous, smooth; leathery. Venation pattern: Parallel. Color: Developing and fully expanded leaves, upper surface: 143A; venation, similar to lamina. Developing and fully expanded leaves, lower surface: 143C; venation, similar to lamina.

*Bulbs.*—Diameter: About 10 cm to 20 cm. Texture: Smooth. Color: Close to 155D.

Flower description:

*Flowering habit.*—Terminal single flowers arranged on a raceme on long, mostly erect and strong flowering stems. Flowers slightly fragrant; tepals not persistent; gynoecium persistent. Flowers face mostly upright.

*Natural flowering season.*—Plants flower in June and July in The Netherlands. Plants can be flowered year-round in the greenhouse and forced to bloom about 65 days after planting bulbs.

*Flower longevity on the plant.*—About 15 to 20 days.

*Flower buds.*—Length: About 7.3 cm. Diameter: About 2.5 cm. Circumference: About 6.2 cm. Shape: Lanceolate. Texture: Slightly pubescent. Color: 65C; sutures, 149B.

*Flowers.*—Quantity of flowers per flowering stem: Freely flowering; larger bulbs will produce plants with about ten flowers per flowering stem. Shape: Funnel-shaped. When fully opened, flowers flatten and reflex slightly. Diameter: About 12.5 cm. Depth (height): About 4 cm.

*Perianth.*—Quantity/arrangement: Six tepals per flower; imbricate. Tepal length, inner tepals: About 7.8 cm. Tepal length, outer tepals: About 8 cm. Tepal width, inner tepals: About 4.7 cm. Tepal width, outer tepals: About 3.6 cm. Tepal shape: Lanceolate. Tepal apex: Acute. Tepal margin: Entire. Tepal texture, upper and lower surfaces: Smooth, glabrous. Tepal color: When opening, upper surface: 55B. When opening, lower surface: 55C. Fully opened, upper surface: 55A; color becoming closer to 54C. Fully opened, lower surface: 55C.

*Pedicels.*—Angle: About 50° to 70° from vertical. Strength: Strong. Length: About 4 cm. Diameter: About 1.5 cm. Texture: Smooth, glabrous. Color: 144A.

*Reproductive organs.*—Stamens: Quantity per flower: Six. Filament length: About 5 cm. Filament color: 155B. Anther length: About 7 mm. Anther color: 24A. Pollen color: 24B. Pistils: Quantity per flower: One. Style length: About 4 cm. Style color: 145C. Stigma length: About 4 mm. Stigma color: 72B. Fruits: Length: About 2.2 cm. Diameter: About 2.5 cm. Color: 144A.

*Seed produced.*—None viable.

Disease/pest resistance: Resistance to pathogens and pests common to Asiatic Hybrid Lilies has not been determined.

It is claimed:

1. A new and distinct cultivar of Lily plant named 'Tiny Icon', as illustrated and described.

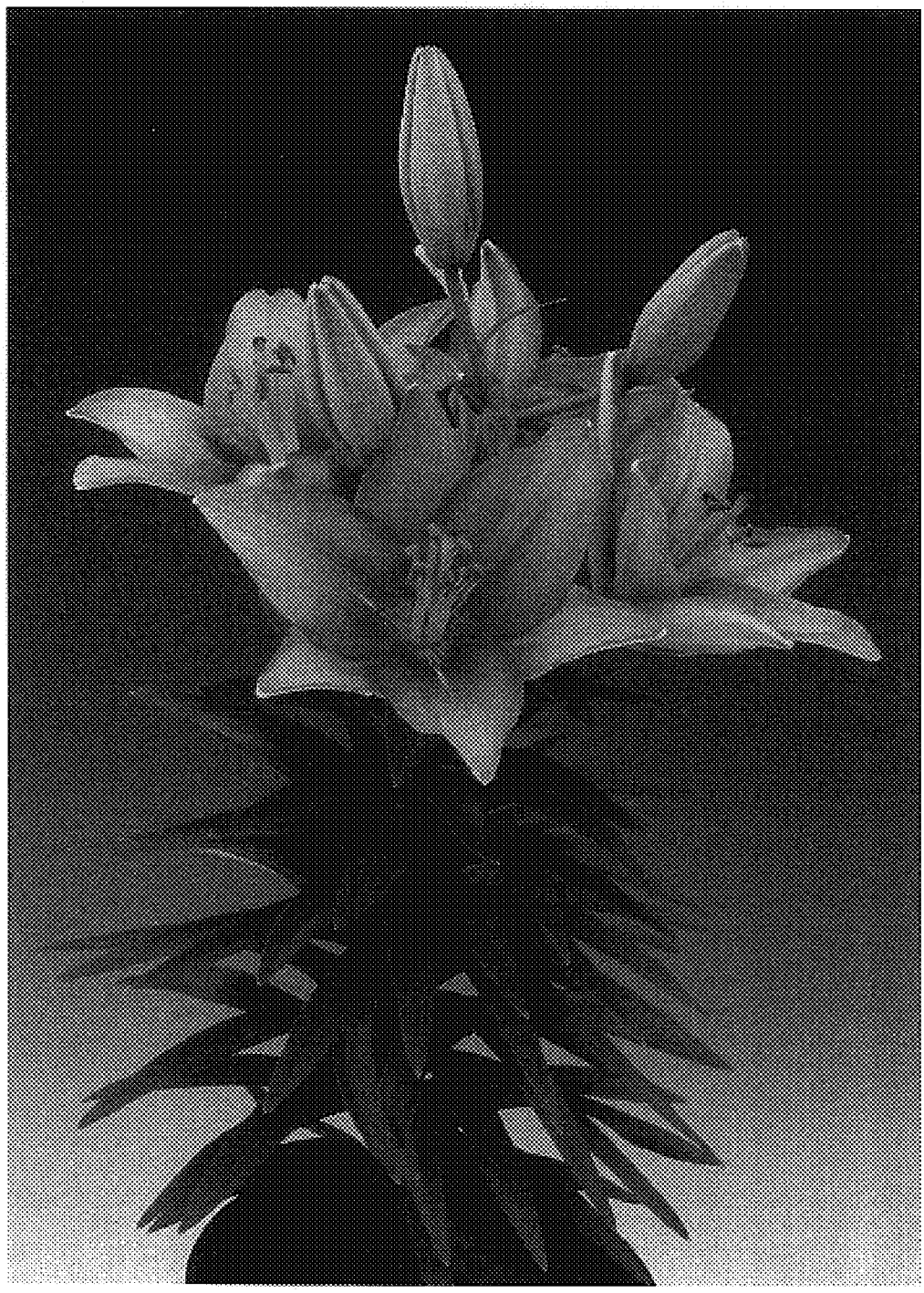

* * * * *